US009932366B2

(12) United States Patent
Choe et al.

(10) Patent No.: US 9,932,366 B2
(45) Date of Patent: Apr. 3, 2018

(54) METHOD FOR USING NANOPARTICLES AS NUCLEATION AGENTS FOR THE CRYSTALLIZATION OF PROTEINS

(71) Applicant: UNIVERSITY OF SEOUL INDUSTRY COOPERATION FOUNDATION, Seoul (KR)

(72) Inventors: Jungwoo Choe, Seoul (KR); Inhee Choi, Seoul (KR)

(73) Assignee: UNIVERSITY OF SEOUL INDUSTRY COOPERATION FOUNDATION (KR)

(*) Notice: Subject to any disclaimer, the term of this patent is extended or adjusted under 35 U.S.C. 154(b) by 29 days.

(21) Appl. No.: 15/287,444

(22) Filed: Oct. 6, 2016

(65) Prior Publication Data
US 2017/0101436 A1    Apr. 13, 2017

(30) Foreign Application Priority Data

Oct. 7, 2015 (KR) .................... 10-2015-0140966
Mar. 28, 2016 (KR) .................... 10-2016-0037077

(51) Int. Cl.
C30B 7/00 (2006.01)
C07K 1/30 (2006.01)
C07K 14/32 (2006.01)

(52) U.S. Cl.
CPC ............ *C07K 1/306* (2013.01); *C07K 14/32* (2013.01); *C30B 7/00* (2013.01); *C07B 2200/13* (2013.01)

(58) Field of Classification Search
CPC ............ C30B 7/00; C30B 29/54; C30B 29/58
See application file for complete search history.

(56) References Cited

PUBLICATIONS

F. Hodzhaoglu et al., 'Gold nanoparticles induce protein crystallization', Cryst. Res. Technol. 43, No. 6, 588-593 (2008).
A. Cacciuto et. al., "Onset of heterogeneous crystal nucleation in colloidal suspensions", Nature. vol. 428, Mar. 25, 2004.
Diana Ribeiro et. al., "Use of Gold Nanoparticles as Additives in Protein Crystallization", Cryst. Growth Des. 2014, 14, 222-227.
Nanoprobes E-News, Jul. 25, 2009, vol. 10, No. 7, 7 pages.
Ribeiro "Using Gold Nanoparticles in Protein Crystallography: Studies in crystal growth and derivatization," Faculdade de Ciências e Tecnologia, Sep. 2012, Dissertation for the Master Degree in Structural and Functional Biochemistry, 113 pages.

*Primary Examiner* — Robert M Kunemund
(74) *Attorney, Agent, or Firm* — Sheridan Ross P.C.

(57) ABSTRACT

The present invention relates to a method for the crystallization of protein using nanoparticles as nucleation agents. Precisely, the inventors performed the crystallization of such proteins as *Bacillus subtilis* YesR, chicken egg white lysozyme, bovine serum albumin, *Alicyclobacillus acidocaldarius* acetyl-CoA carboxylase, and *Listeria monocytogenes* hypothetical protein which have his-tag at amino terminal by using gold nanoparticles in diverse sizes and shapes in the presence of $Ni^{2+}$ ions. As a result, it was confirmed that the chance of successful crystallization was higher with the gold nanoparticles than without the gold nanoparticles and the various crystallization conditions were successfully screened. Therefore, the method for inducing nucleation of the invention can be advantageously used for the disclosure of protein structure by increasing the chance of successful crystallization of protein.

12 Claims, 18 Drawing Sheets

[FIG. 1]
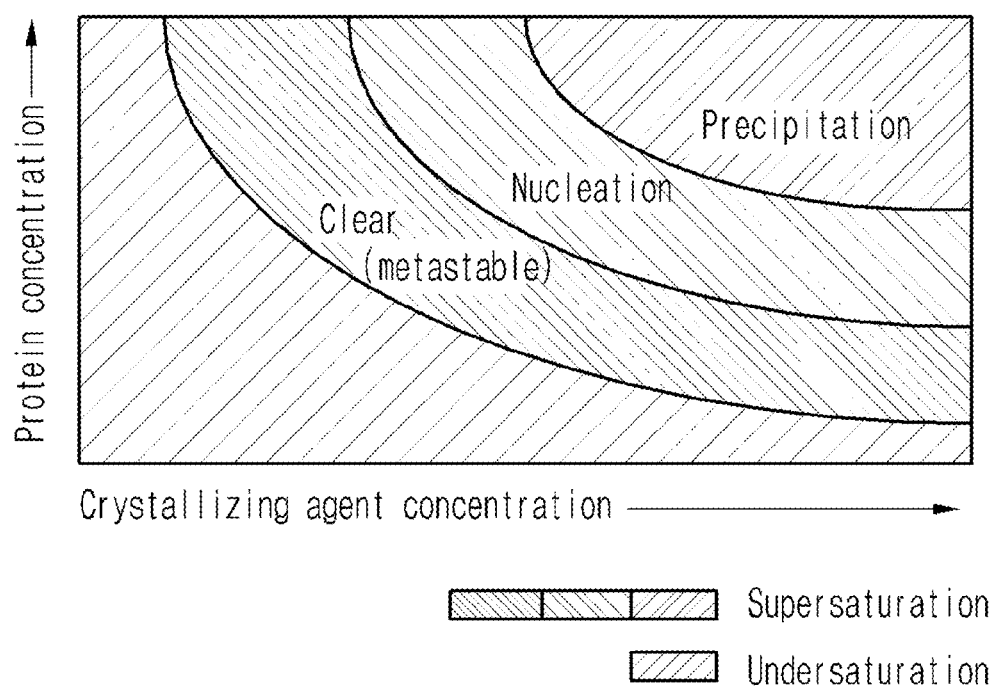

[FIG. 2]
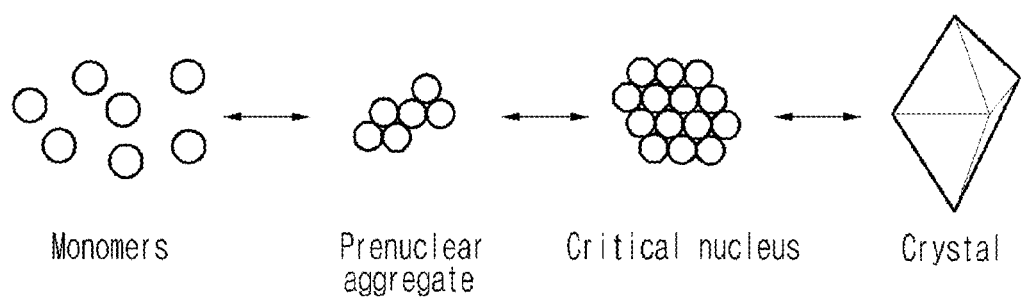

[FIG. 3]
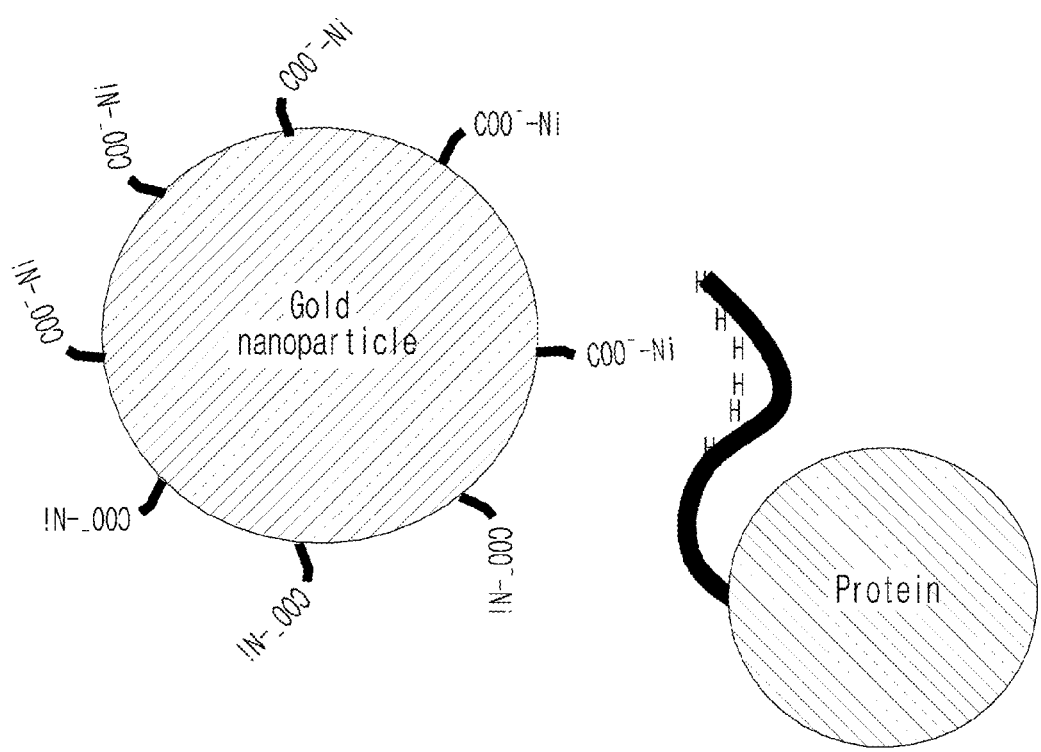

[FIG. 4]
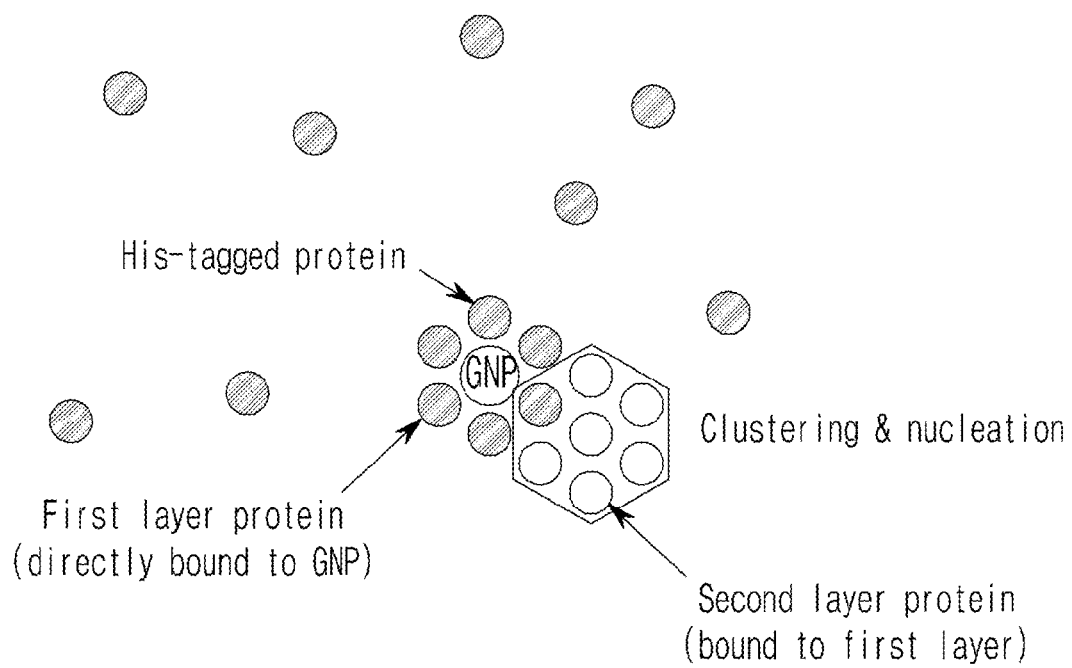

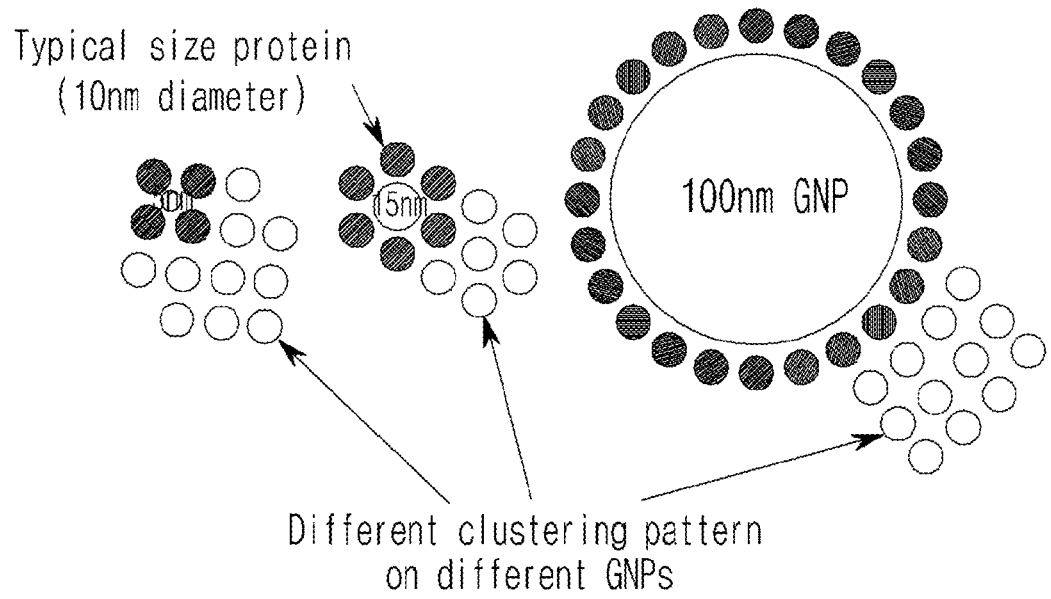
[FIG. 5]

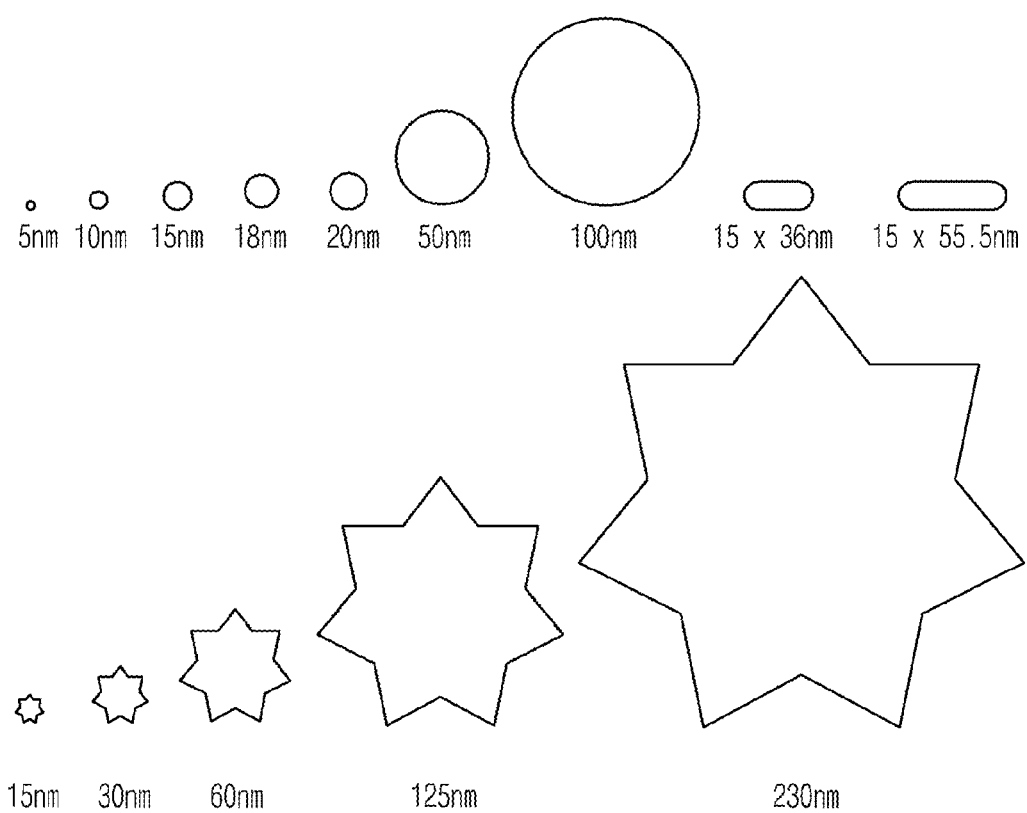
[FIG. 6]

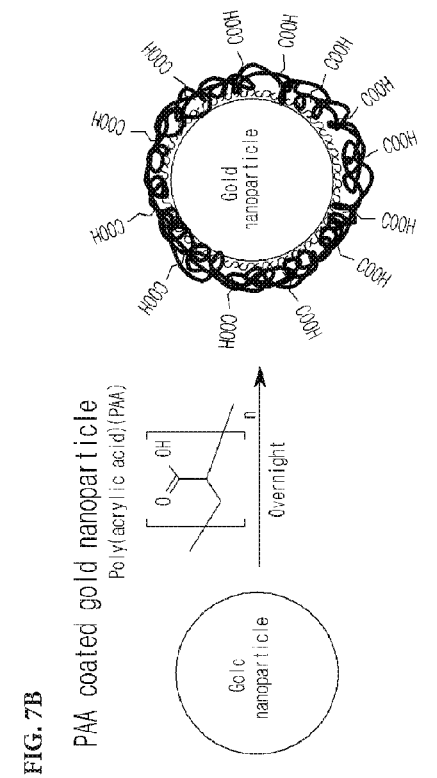
FIG. 7A
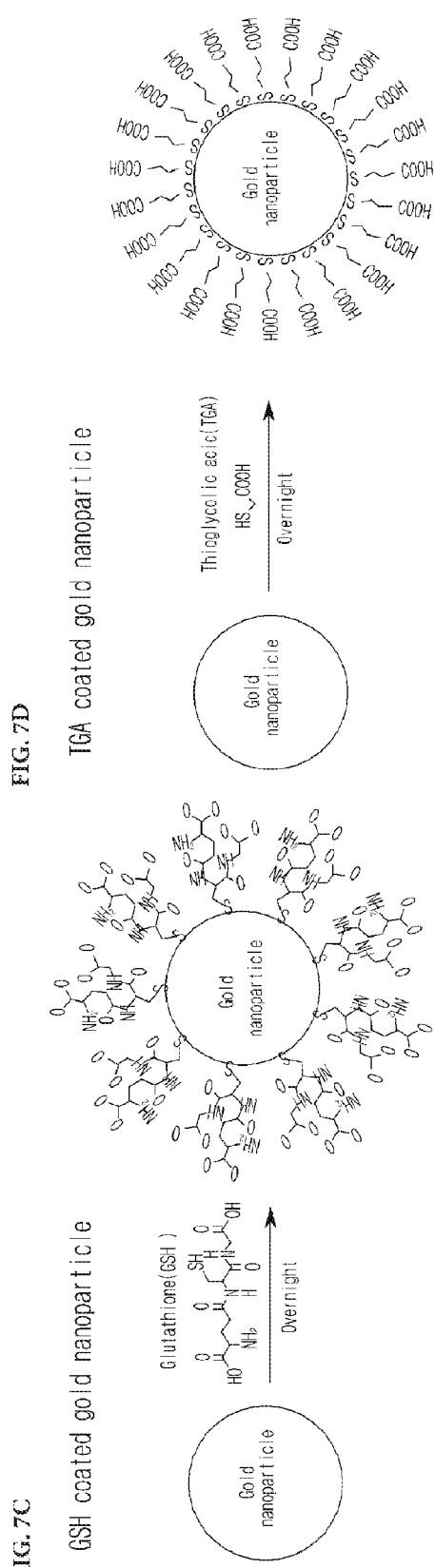
FIG. 7B
FIG. 7D
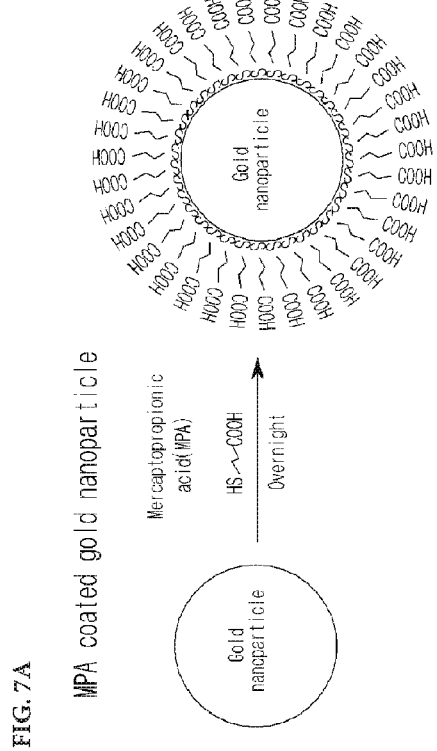
FIG. 7C

[FIG. 8]
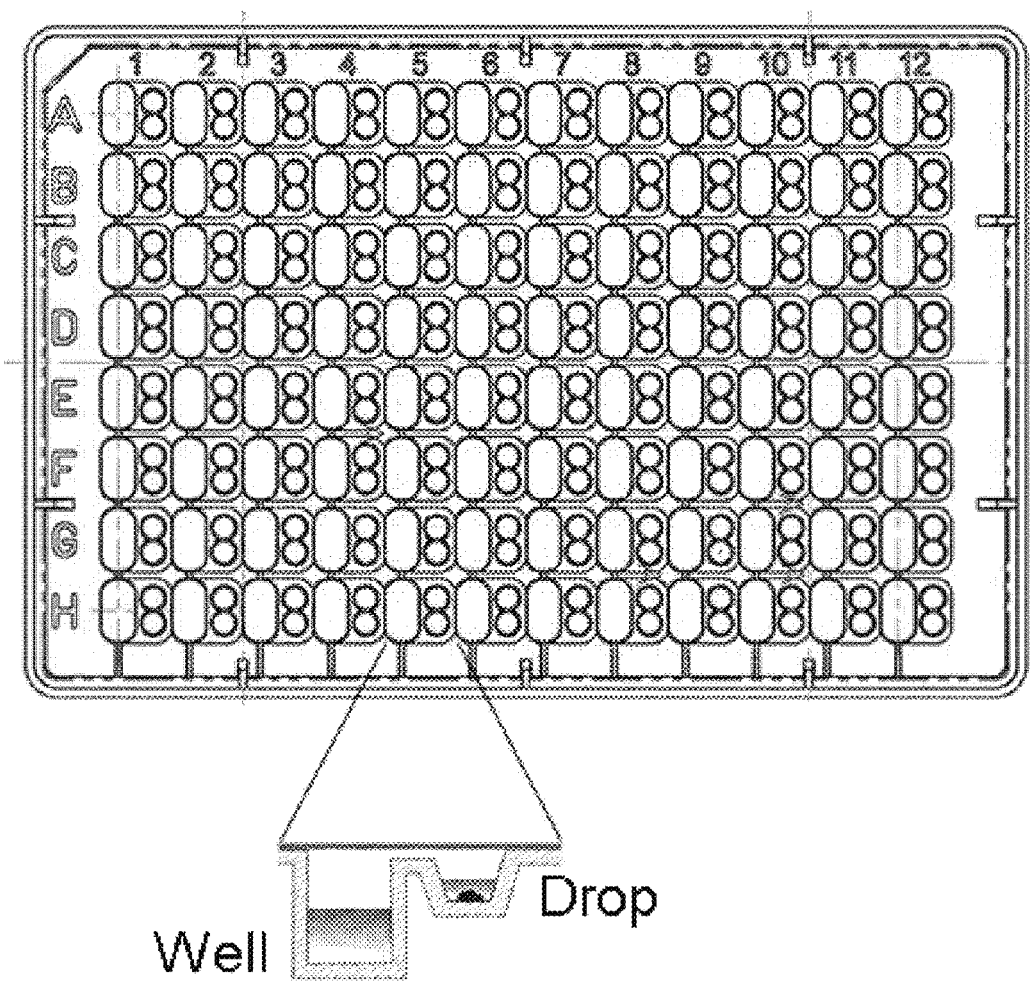

| Cond. # | Well | Salt | Buffer | Precipitant |
|---|---|---|---|---|
| 1 | A1 | 0.2 M Potassium Sodium Tartrate | | 20% (w/v) PEG 3350 |
| 2 | A2 | 0.15 M Potassium Bromide | | 30% (w/v) PEG MME 2000 |
| 3 | A3 | 0.2 M Sodium Chloride | 0.1 M Na$_2$HPO$_4$:Citric Acid pH 4.2 | 20% (w/v) PEG 8000 |
| 4 | A4 | | 0.1 M Sodium Acetate:Acetic Acid pH 4.5 | 0.8 M NaH$_2$PO$_4$/1.2 M K$_2$HPO$_4$ |
| 5 | A5 | 0.2 M Lithium Sulfate | 0.1 M CAPS:NaOH pH 10.5 | 1.2 M NaH$_2$PO$_4$/0.8 M K$_2$HPO$_4$ |
| 6 | A6 | | 0.1 M Sodium Cacodylate:HCl pH 6.5 | 1.26 M Ammonium Sulfate |
| 7 | A7 | 0.2 M Sodium Chloride | 0.1 M Na$_2$HPO$_4$:Citric Acid pH 4.2 | 10% (w/v) PEG 3000 |
| 8 | A8 | 0.2 M Potassium Formate pH 7.3 | | 20% (w/v) PEG 3350 |
| 9 | A9 | | 0.1 M Sodium Citrate:HCl pH 5 | 20% (w/v) PEG 6000 |
| 10 | A10 | 0.2 M Ammonium Nitrate pH 6.3 | | 20% (w/v) PEG 3350 |
| 11 | A11 | 0.2 M Lithium Chloride | | 20% (w/v) PEG 3350 |
| 12 | A12 | | 0.1 M Sodium Citrate:Citric Acid pH 5.5 | 40% (v/v) PEG 600 |
| 13 | B1 | | 0.1M MES:NaOH pH 6.5 | 12% (w/v) PEG 20,000 |
| 14 | B2 | 0.2 M Potassium Acetate | | 20% (w/v) PEG 3350 |
| 15 | B3 | 0.2 M Ammonium Citrate Dibasic | | 20% (w/v) PEG 3350 |
| 16 | B4 | | 1.8 M NaH$_2$PO$_4$/K$_2$HPO$_4$ pH 8.2 | |
| 17 | B5 | 0.2 M Ammonium Sulfate | 0.1 M Sodium Cacodylate:HCl pH 6.5 | 30% (w/v) PEG 8000 |
| 18 | B6 | 0.2 M Sodium Formate | | 20% (w/v) PEG 3350 |
| 19 | B7 | | 0.1 M Bis-Tris Propane:HCl pH 7.0 | 2.8 M Sodium Acetate pH 7.0 |
| 20 | B8 | | | 1.1 M Malonic Acid, 0.15 M Ammonium Citrate Tribasic, 0.072 M Succinic Acid, 0.18 M DL-Malic Acid, 0.24 M Sodium Acetate, 0.3 M Sodium Formate, 0.096 M Ammonium Tartrate Dibasic, Final pH 7.0 |
| 21 | B9 | 1.0 M Ammonium Sulfate | 0.1 M Bis-Tris:HCl pH 5.5 | 1% (w/v) PEG 3350 |
| 22 | B10 | 1.1 M Sodium Malonate pH 7.0 | 0.1 M HEPES:NaOH pH 7.0 | 0.5% (v/v) Jeffamine® ED-2001 pH 7.0 |
| 23 | B11 | 0.2 M Lithium Sulfate | 0.1 M Bis-Tris:HCl pH 6.5 | 25% (w/v) PEG 3350 |
| 24 | B12 | 3.0 M Sodium Chloride | 0.1 M Bis-Tris:HCl pH 5.5 | |
| 25 | C1 | 0.8 M Succinic Acid pH 7.0 | | |
| 26 | C2 | | | 0.64 M Malonic Acid, 0.088 M Ammonium Citrate Tribasic, 0.042 M Succinic Acid, 0.105 M DL-Malic Acid, 0.14 M Sodium Acetate, 0.175 M Sodium Formate, 0.056 M Ammonium Tartrate Dibasic, Final pH 7.0 |
| 27 | C3 | 0.2 M Ammonium Acetate | 0.1 M HEPES:NaOH pH 7.5 | 25% (w/v) PEG 3350 |
| 28 | C4 | 0.2 M Ammonium Citrate Tribasic pH 7.0 | | 20% (w/v) PEG 3350 |
| 29 | C5 | 0.2 M Sodium Citrate | | 20% (w/v) PEG 3350 |
| 30 | C6 | | 0.1 M BICINE:NaOH pH 9 | 20% (w/v) PEG 6000 |
| 31 | C7 | | 0.1 M Tris:HCl pH 8.5 | 1.5 M Ammonium Phosphate Dibasic |
| 32 | C8 | | 0.1 M Bis-Tris Propane:HCl pH 7.0 | 1.8 M Magnesium Sulfate |
| 33 | C9 | 0.2 M Sodium Flouride | | 20% (w/v) PEG 3350 |
| 34 | C10 | 0.2 M Sodium Nitrate | | 20% (w/v) PEG 3350 |
| 35 | C11 | | 0.1 M Bis-Tris Propane:HCl pH 7.0 | 1.3 M Ammonium Tartrate Dibasic |
| 36 | C12 | | 0.1 M Tris:HCl pH 8.5 | 1.4 M Ammonium Tartrate Dibasic |
| 37 | D1 | | 0.1 M Tris:HCl pH 8.5 | 1.5 M Ammonium Sulfate |
| 38 | D2 | 0.2 M Lithium Sulfate | 0.1 M Tris:HCl pH 8.5 | 1.26 M Ammonium Sulfate |
| 39 | D3 | 0.2 M Lithium Sulfate | 0.1 M CAPS:NaOH pH 10.5 | 2.0 M Ammonium Sulfate |
| 40 | D4 | 0.2 M Calcium Acetate | 0.1 M Sodium Acetate:Acetic Acid pH 4.5 | 30% (v/v) PEG 400 |
| 41 | D5 | | 0.1 M Tris:HCl pH 8.5 | 3.0 M Sodium Chloride |
| 42 | D6 | 2.8 M Sodium Acetate pH 7.0 | | |
| 43 | D7 | 1.1 M Ammonium Tartrate Dibasic pH 7.0 | | |
| 44 | D8 | 0.2 M Potassium Nitrate pH 6.9 | | 20% (w/v) PEG 3350 |
| 45 | D9 | 1 M Lithium Chloride | 0.1 M Sodium Citrate:HCl pH 4 | 20% (w/v) PEG 6000 |
| 46 | D10 | 0.2 M Lithium Citrate Tribasic | | 20% (w/v) PEG 3350 |
| 47 | D11 | | 0.1 M Tris:HCl pH 8.5 | 1.5 M Lithium Sulfate |
| 48 | D12 | 0.2 M Ammonium Sulfate | | 20% (w/v) PEG 3350 |

FIG. 9

| Cond.# | Well | Salt | Buffer | Precipitant |
|---|---|---|---|---|
| 49 | E1 | | 0.1 M Bis-Tris Propane:HCL pH 7.0 | 1.8 M Sodium Acetate pH 7.0 |
| 50 | E2 | | 0.1 M Bis-Tris Propane:HCL pH 7.0 | 3.2 M Sodium Chloride |
| 51 | E3 | | 0.1 M Bis-Tris Propane:HCL pH 7.0 | 1.5 M Lithium Sulfate |
| 52 | E4 | 1.6 M Ammonium Sulfate | 0.1 M MES:NaOH pH 6.5 | 10% (v/v) Dioxane |
| 53 | E5 | 0.2 M Lithium Sulfate | 0.1 M Sodium Acetate:Acetic Acid pH 4.5 | 30% (w/v) PEG 8000 |
| 54 | E6 | | 0.1 M Sodium Acetate:Acetic Acid pH 4.5 | 1 M Ammonium Phosphate Dibasic |
| 55 | E7 | 0.2 M Lithium Sulfate | 0.1 M Na$_2$HPO:Citric Acid pH 4.2 | 20% (w/v) PEG 1000 |
| 56 | E8 | | 0.1 M CHES:NaOH pH 9.5 | 20% (w/v) PEG 8000 |
| 57 | E9 | | 0.1 M CHES:NaOH pH 9.5 | 1.0 M Sodium Citrate |
| 58 | E10 | | 0.1 M Na$_2$HPO:Citric Acid pH 4.2 | 1.6 M NaH$_2$PO$_4$/0.4 M K$_2$HPO$_4$ |
| 59 | E11 | 0.2 M Magnesium Chloride | 0.1 M Sodium Cacodylate:HCl pH 6.5 | 10% (w/v) PEG 3000 |
| 60 | E12 | 0.2 M Lithium Sulfate | 0.1 M Sodium Cacodylate:HCl pH 6.5 | 30% (v/v) PEG 400 |
| 61 | F1 | 0.2 M Sodium Chloride | 0.1 M Imidazole:HCl pH 8.0 | 1.0 M Ammonium Phosphate Dibasic |
| 62 | F2 | | 0.1 M Bis-Tris:HCl pH 6.5 | 3.0 M Sodium Chloride |
| 63 | F3 | | 0.1 M HEPES:NaOH pH 7.5 | 3.0 M Sodium Chloride |
| 64 | F4 | | | 1.0 M NaH$_2$PO$_4$/K$_2$HPO$_4$ pH 6.9 |
| 65 | F5 | 0.02 M Magnesium Chloride | 0.1 M HEPES:NaOH pH 7.5 | 22% (w/v) Polyacrylic Acid 5100 |
| 66 | F6 | 0.2 M Sodium Malonate pH 7.0 | | 20% (w/v) PEG 3350 |
| 67 | F7 | 0.15 M DL-Malic Acid pH 7.0 | | 20% (w/v) PEG 3350 |
| 68 | F8 | 0.2 M Ammonium Phosphate Monobasic | 0.1 M TRIS:HCl pH 8.5 | 50% (w/v) MPD |
| 69 | F9 | | 0.1 M HEPES:NaOH pH 7 | 10% (w/v) PEG 6000 |
| 70 | F10 | | | 24% (w/v) PEG 1500, 20% (v/v) glycerol |
| 71 | F11 | 0.2 M Sodium Tartrate Dibasic | | 20% (w/v) 3350 |
| 72 | F12 | 0.2 M Lithium Nitrate | | 20% (w/v) 3350 |
| 73 | G1 | 0.2 M Sodium Phosphate Dibasic | | 20% (w/v) 3350 |
| 74 | G2 | | 0.1 M Tris:HCl pH 8.5 | 2.4 M Ammonium Phosphate Dibasic |
| 75 | G3 | 0.2 M Sodium Chloride | 0.1 M Imidazole:HCl pH 8.0 | 0.4 M NaH$_2$PO$_4$/1.6 M K$_2$HPO$_4$ |
| 76 | G4 | 0.2 M Calcium Acetate | 0.1 M MES:NaOH pH 6.0 | 10% (v/v) 2-Propanol |
| 77 | G5 | 0.2 M Sodium Chloride | 0.1 M CHES:NaOH pH 9.5 | 1.26 M Ammonium Sulfate |
| 78 | G6 | 0.2 M Sodium Chloride | 0.1 M Sodium Citrate:Citric Acid pH 5.5 | 1.0 M Ammonium Phosphate Dibasic |
| 79 | G7 | | 0.1 M Tris-HCl pH 7.0 | 15% (v/v) Ethanol |
| 80 | G8 | | 0.1 M Tris-HCl pH 7.0 | 20% (w/v) PEG 1000 |
| 81 | G9 | 0.2 M Sodium Chloride | 0.1 M Na$_2$HPO$_4$:KH$_2$PO$_4$ pH 6.2 | 20% (w/v) PEG 1000 |
| 82 | G10 | 0.2 M Sodium Chloride | 0.1 M CAPS:NaOH pH 10.5 | 20% (w/v) PEG 8000 |
| 83 | G11 | | 0.1 M HEPES:NaOH pH 7.0 | 30% (v/v) Jeffamine® ED-2001 pH 7.0 |
| 84 | G12 | 0.2 M Calcium Chloride | 0.1 M Bis-Tris:HCl pH 5.5 | 45% (v/v) MPD |
| 85 | H1 | 0.2 M Calcium Chloride | 0.1 M Bis-Tris:HCl pH 6.5 | 45% (v/v) MPD |
| 86 | H2 | 0.2 M Potassium Chloride | 0.05 M HEPES:NaOH pH 7.5 | 35% (v/v) PentaerythritolPropoxylate (5/4PO/OH) |
| 87 | H3 | 0.2 M Trimethylamine N-oxide | 0.1 M Tris:HCl pH 8.5 | 20% (w/v) PEG MME 2000 |
| 88 | H4 | 0.2 M Ammonium Acetate | 0.1 M Tris:HCl pH 8.5 | 25% (w/v) PEG 3350 |
| 89 | H5 | 0.2 M Succinic Acid pH 7.0 | | 15% (w/v) PEG 3350 |
| 90 | H6 | | 0.1 M Sodium Citrate:HCl pH 4 | 0.8 M Ammonium Sulfate |
| 91 | H7 | | 0.1 M BICINE:NaOH pH 9 | 10% (w/v) PEG 20000, 2% (v/v) Dioxane |
| 92 | H8 | 0.2 M Magnesium Chloride | 0.1 M HEPES:NaOH pH 7.5 | 30% (v/v) PEG 400 |
| 93 | H9 | | 0.1 M Sodium Acetate:HCl pH 4.6 | 2.5 M Ammonium Sulfate |
| 94 | H10 | 0.2 M Sodium Chloride | | 20% (w/v) PEG 3350 |
| 95 | H11 | | 0.1 M Tris:HCl pH 8.5 | 2.5 M Ammonium Sulfate |
| 96 | H12 | 0.2 M Zinc Acetate | 0.1 M Sodium Acetate:Acetic Acid pH 4.5 | 10% (w/v) PEG 3000 |

# METHOD FOR USING NANOPARTICLES AS NUCLEATION AGENTS FOR THE CRYSTALLIZATION OF PROTEINS

CROSS-REFERENCE TO RELATED APPLICATIONS

This application claims the benefit of Korean Patent Application No. 10-2015-0140966 filed Oct. 7, 2015, and Korean Patent Application No. 10-2016-0037077 filed Mar. 28, 2016, the entire contents of each of which are incorporated herein by reference.

BACKGROUND OF THE INVENTION

1. Field of the Invention

The present invention relates to a method for the crystallization of proteins using nanoparticles as nucleation agents. Particularly, the invention relates to a method to increase the opportunity of crystallization of protein by inducing nucleation of protein particularly by conjugating His-tag to protein in order for the protein to be combined with nanoparticles having carboxyl group using $Ni^{2+}$ ions as a linker.

2. Description of the Related Art

X-ray crystallography is a method to provide an important clue for the understanding of functions of biopolymers including proteins through structure determination in the field of structural biology. The structures of 89% of the total biopolymers identified so far were determined by X-ray crystallography. Structure determination using X-ray crystallography is accomplished by the following steps such as protein over-expression, purification, crystallization, collection of X-ray diffraction data, and structure determination. Supersaturation of protein, which is necessary for protein crystallization, can be induced by increasing the concentration of protein or by increasing a reagent to induce protein precipitation (FIG. 1). However, the concentrations of protein and the precipitation solution have to be precise and suitable for inducing nucleation. If the concentration is too high, an amorphous precipitate would be generated. On the other hand, if the concentration is too low, the solution would stay in metastable state so that a precipitate would not be generated at all. Spontaneous protein crystallization is composed of two steps, which are nucleation and crystal growth (FIG. 2). For the formation of stable nucleation, proteins existing as a monomer in the solution have to be gathered together to form a cluster. Once nucleation occurs, crystal growth continues as long as the protein stays in the supersaturation state. Factors affecting the crystallization of protein such as precipitants, pH, temperature, pressure, and gravity, have been studied. However, the conditions for the crystallization of each protein vary (Adachi, H. et al., Temperature-screening system for determining protein crystallization conditions. Jpn. J. Appl. Phys. 44, 4080-4083, 2005), and many trials and errors to find out proper crystallization conditions for each protein are still needed. In the course of crystallization, nucleation is the most important step. So, inducing nucleation can be an important way to increase the chance of successful crystallization of protein.

Significant advances have been made in many stages of X-ray crystallography due to the technological developments of modern biology. However, success in crystallization of protein is still depends on the time consuming trial-and-error process.

Therefore, the present invention provides a method for using nanoparticles in order to help nucleation that plays an important role in protein crystallization. In the previous studies, induction of nucleation using gold nanoparticles has been reported. However, the method is a non-selective method using the conjugation between gold particles and sulfur atoms included in cysteine or methionine residues exposed on the surface of protein. So, this method can only be applied to those proteins that have sulfur exposed on the surface. This method also has a problem of non-selective conjugation between gold particles with other impurity proteins in addition to the target proteins. Thus, it was difficult to induce nucleation of target protein with high purity that could be a great help for the crystallization of protein. The present inventors confirmed that the method for inducing nucleation using gold nanoparticles could be effectively used as a method for the crystallization of protein with high purity, leading to the completion of the invention.

SUMMARY OF THE INVENTION

It is an object of the present invention to provide a method for the crystallization of protein using gold nanoparticles as nucleation agents.

To achieve the above object, the present invention provides a method of nucleation for the crystallization of protein comprising the step of combining nanoparticles coated with carboxyl group and proteins having his-tag in the presence of $Ni^{2+}$ ions.

The present invention also provides a method for inducing selective conjugation of target protein and controlling the orientation of conjugation for the crystallization of protein by mixing nanoparticles coated with carboxyl group and proteins having his-tag in the presence of $Ni^{2+}$ ions.

The present invention further provides a kit for the crystallization of protein containing the followings:
1) a resin mixed with nanoparticles coated with carboxyl group containing $Ni^{2+}$; and
2) a protein having his-tag on the surface thereof.

ADVANTAGEOUS EFFECT

Even though protein crystallization is a necessary step for the structure determination using X-ray crystallography, the prediction is difficult and the steps take a long time. Nucleation using gold nanoparticles has an effect of increasing the chance of successful crystallization by facilitating nucleation, the most important step in the crystallization. Higher success rate of crystallization leads to a shorter structure determination time and even make possible of protein structure determination which failed in the previous trials because of unsuccessful crystallization.

Unlike the previous method based on the conjugation between gold nanoparticles and sulfur originated from cysteine or methionine exposed on the surface of protein, the method of the invention attaches His-tag on a target surface and uses $Ni^{2+}$ ions as a linker for the conjugation onto nanoparticles having carboxyl group. As a result, the nanoparticles bind fastly and strongly to the protein and the nanoparticles bind selectively to the only those proteins that have his-tag to induce nucleation. It is also possible to control the direction of protein toward nanoparticles by changing the position of his-tag on target protein and the direction toward nanoparticles. In this invention, the present inventors studied the effect of the size, shape, and concentration of nanoparticles on nucleation for the protein crystallization. The inventors confirmed at last that the method of the invention for the crystallization of protein using nanoparticles as nucleation agents can be effectively used for the protein structure determination by increasing the success rate of protein crystallization.

BRIEF DESCRIPTION OF THE DRAWINGS

The application of the preferred embodiments of the present invention is best understood with reference to the accompanying drawings, wherein:

FIG. 1 is a diagram illustrating the phase changes of protein according to the crystallization inducing compounds and the concentration thereof.

FIG. 2 is a diagram illustrating the step necessary for the crystallization of a single protein molecule.

FIG. 3 is a diagram illustrating the conjugation between gold nanoparticles coated with carboxyl group and protein having his-tag in the presence of $Ni^{2+}$ ions.

FIG. 4 is a diagram illustrating the inducement of nucleation for the crystallization by gold nanoparticles that helps the clustering of proteins having His-tag via the conjugation shown in FIG. 3.

FIG. 5 is a diagram illustrating that gold nanoparticles in different sizes can induce nucleation in diverse shapes which are advantageous for the crystallization.

FIG. 6 is a diagram illustrating the comparative sizes and shapes of gold nanoparticles used for the protein crystallization.

FIGS. 7A-7H are diagrams illustrating the diverse methods for coating the surface of nanoparticles so as for them to have carboxyl group on the surface. FIG. 7A MPA coated goal nanoparticle; FIG. 7B PAA coated gold nanoparticle; FIG. 7C GSH coated gold nanoparticle; FIG. 7D TGA coated gold nanoparticle; FIG. 7E cysteine coated gold nanoparticle; FIG. 7F mecaptobenzoic acid coated gold nanoparticle; FIG. 7G D-penicillamine coated gold nanoparticle; and FIG. 7H DHLA coated gold nanoparticle.

FIG. 8 is a diagram illustrating the structure of 96-well sitting drop plate used for the protein crystallization.

FIG. 9 and FIG. 10 are diagrams illustrating the compositions of 96 MCSG-2T crystallization solutions used for the protein crystallization.

DESCRIPTION OF THE PREFERRED EMBODIMENTS

Figure 7E:
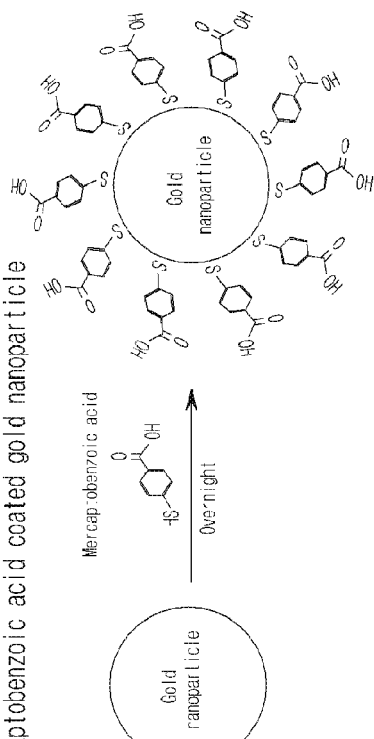
Figure 7G:
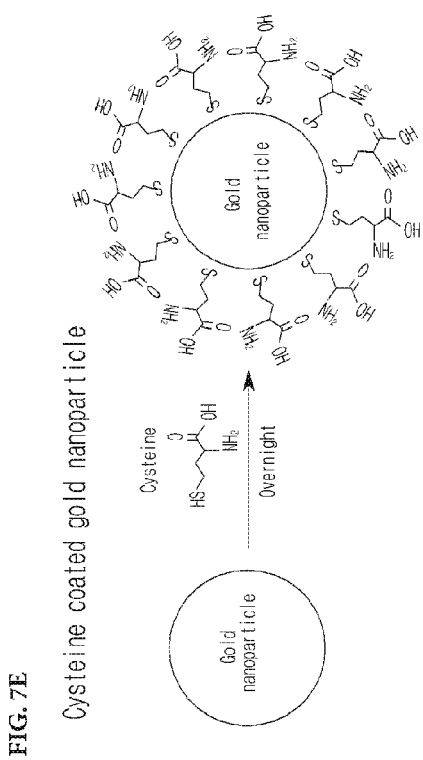
Figure 7F:
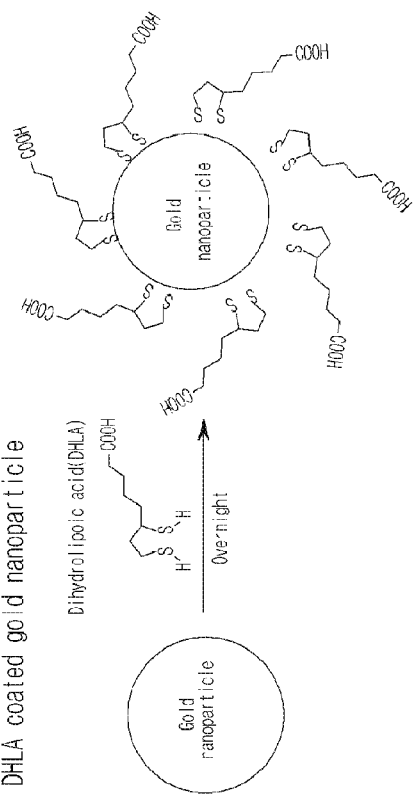
Figure 7H:
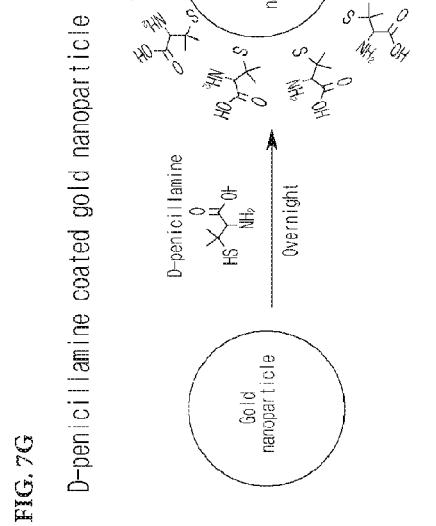

Hereinafter, the present invention is described in detail.

The present invention provides a method for inducing nucleation for the crystallization of protein comprising the step of mixing nanoparticles coated with carboxyl group and proteins having his-tag in the presence of $Ni^{2+}$ ions.

The nanoparticles herein can be prepared in different sizes and shapes with different compositions, which are exemplified by platinum nanoparticles, silver nanoparticles, magnetic nanoparticles, polymer nanoparticles, and gold nanoparticles. In a preferred embodiment of the present invention, gold nanoparticles are preferably used, which can be in the shape of sphere, rod, and star. If the gold nanoparticles in the shape of sphere are used, the diameter of the particle is preferably 5~100 nm. If the particle is in the shape of rod, it is preferably 36~55.5 nm in length and 15 nm in diameter. If the particle is in the shape of star, the diameter is preferably 15~230 mm.

For the crystallization, preferably $10^3$~$10^7$ nanoparticles are used, and more preferably $10^4$ nanoparticles are used.

The surface of the nanoparticle is preferably coated with carboxyl group using a carboxyl group-rich organic molecule. The carboxyl group-rich organic molecule is preferably selected from the group consisting of citrate, mercaptoundecanoic acid (MUA), mercaptopropionic acid (MPA), poly acrylic acid, glutathione (GSH), thioglycolic acid (TGA), cysteine, mercaptobenzoic acid, D-penicillamine, and dihydrolipoic acid (DHLA), and is more preferably citrate according to a preferred embodiment of the present invention.

When citrate is used as a surface stabilizer with carboxyl group in the course of nanoparticle synthesis, the surface of the nanoparticle is coated with carboxyl group and the carboxyl group herein is conjugated to $Ni^{2+}$ ions and then the $Ni^{2+}$ ions are conjugated with the protein having his-tag (FIG. 3). The protein having his-tag is often used for the purification. The conjugation with carboxyl group, $Ni^{2+}$ ions, and his-tag in that order provides a strong and selective conjugation between protein and nanoparticles. Compared with the conventional method which is a non-selective method using the conjugation between gold particles and sulfur included in the cysteine or methionine exposed on the surface of protein, the method of the invention has a few more advantages. First, the method of the invention is characterized by the selective conjugation targeting the protein having his-tag alone, and other proteins around, considered as impurities, are excluded from the conjugation. Second, the direction of the protein toward the nanoparticles for the conjugation is consistent and the direction can be controlled by re-locating his-tag. Lastly, not only gold nanoparticles but also other nanoparticles in diverse compositions and shapes can be coated with carboxyl group on their surface.

For the preparation of the nanoparticles, an additional step of treating the surface can be included and at this time the surface treatment can be achieved by using MUA, MPA, PAA, GSH, TGA, cysteine, mercaptobenzoic acid, D-penicillamine, and DHLA.

The conjugation between the protein having his-tag and nanoparticles brings the effect of clustering proteins around the nanoparticles. The protein suitable for the conjugation with the nanoparticles can grow to a proper size by being conjugated with other proteins and can act as a nucleus necessary for the crystallization (FIG. 4). From the analysis of the crystal structure which had been already disclosed, it was confirmed that the proteins could be stacked differently for forming the crystal and the conjugation between nanoparticles and proteins could be diverse according to the sizes and shapes of nanoparticles. This was because the sizes of the nanoparticles were similar to those of the proteins and the different sizes and shapes of the nanoparticles provided different curvatures (FIG. 5). Therefore, using different nanoparticles can increase the chance of producing the most proper nucleus for the crystallization of a specific protein.

The protein herein is preferably the protein containing his-tag at the concentration of 10 mg/ml, and the count rate of protein and nanoparticles is preferably $1:10^7 \sim 1:10^{13}$, and more preferably $1:10^{10}$.

In a preferred embodiment of the present invention, the present inventors synthesized gold nanoparticles containing carboxyl group in different sizes and shapes, with which the inventors performed the crystallization of such proteins as *Bacillus subtilis* YesR, chicken egg white lysozyme, bovine serum albumin, *Alicyclobacillus acidocaldarius* acetyl-CoA carboxylase, and *Listeria monocytogenes* hypothetical protein which have his-tag at amino terminal in the presence of $Ni^{2+}$ ions. As a result, compared with the control without gold nanoparticles, the chance of successful crystallization was increased with the gold nanoparticles and diverse crystallization conditions were identified. Therefore, the method for inducing nucleation of the invention can be advantageously used for the disclosure of protein structure by increasing the chance of successful crystallization of protein.

The present invention also provides a method for inducing protein orientation for the crystallization of protein containing the step of mixing the nanoparticles coated with carboxyl group with the proteins having his-tag in the presence of $Ni^{2+}$ ions.

The nanoparticles herein can be prepared in different sizes and shapes with different compositions, which are exemplified by platinum nanoparticles, silver nanoparticles, magnetic nanoparticles, polymer nanoparticles, and gold nanoparticles. In a preferred embodiment of the present invention, gold nanoparticles are preferably used, which can be in the shape of sphere, rod, and star. If the gold nanoparticles in the shape of sphere are used, the diameter of the particle is preferably 5~100 nm. If the particle is in the shape of rod, it is preferably 36~55.5 nm in length and 15 nm in diameter. If the particle is in the shape of star, the diameter is preferably 15~230 mm.

For the crystallization, preferably $10^3 \sim 10^7$ nanoparticles are used, and more preferably $10^4$ nanoparticles are used.

The surface of the nanoparticle is preferably coated with carboxyl group using a carboxyl group-rich organic molecule. The carboxyl group-rich organic molecule is preferably selected from the group consisting of citrate, mercapundecanoic acid (MUA), mercaptopropionic acid (MPA), poly acrylic acid (PAA), glutathione (GSH), thioglycolic acid (TGA), cysteine, mercaptobenzoic acid, D-penicillamine, and dihydrolipoic acid (DHLA), and is more preferably citrate according to a preferred embodiment of the present invention.

For the preparation of the nanoparticles, an additional step of treating the surface can be included and at this time the surface treatment can be achieved by using MUA, MPA, PAA, GSH, TGA, cysteine, mercaptobenzoic acid, D-penicillamine, and DHLA.

The protein herein is preferably the protein containing his-tag at the concentration of 10 mg/ml, and the count rate of protein and nanoparticles is preferably $1:10^7 \sim 1:10^{13}$, and more preferably $1:10^{10}$.

In a preferred embodiment of the present invention, the present inventors synthesized gold nanoparticles containing carboxyl group in different sizes and shapes, with which the inventors performed the crystallization of such proteins as *Bacillus subtilis* YesR, chicken egg white lysozyme, bovine serum albumin, *Alicyclobacillus acidocaldarius* acetyl-CoA carboxylase, and *Listeria monocytogenes* hypothetical protein which have his-tag at amino terminal in the presence of $Ni^{2+}$ ions. As a result, compared with the control without gold nanoparticles, the chance of successful crystallization was increased with the gold nanoparticles and diverse crystallization conditions were identified. Therefore, the method for inducing nucleation of the invention can be advantageously used for the disclosure of protein structure by increasing the chance of successful crystallization of protein.

The present invention further provides a kit for the crystallization of protein containing the followings:
1) a resin mixed with nanoparticles coated with carboxyl group containing $Ni^{2+}$; and
2) a protein having his-tag on the surface thereof.

The present invention also provides a nucleation agent for the crystallization of protein containing nanoparticles coated with carboxyl group.

Practically and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Synthesis of Gold Nanoparticles

In the course of the crystallization of such proteins having his-tag on their amino terminals as *Bacillus subtilis* YesR, chicken egg white lysozyme, bovine serum albumin, *Alicyclobacillus acidocaldarius* acetyl-CoA carboxylase, and *Listeria monocytogenes* hypothetical protein, the effect of gold nanoparticles was examined. To do so, 14 different gold nanoparticles were synthesized as follows: gold nanoparticles in the shape of sphere having different diameters of 5, 10, 15, 18, 20, 50, and 100 nm, nanoparticles in the shape of rod having different sizes of 15×36 and 15×55.5 nm, and nanoparticles in the shape of star having different diameters of 15, 30, 60, 125, and 230 nm.

<1-1> Synthesis of Gold Nanoparticles in the Shape of Sphere

To synthesize gold nanoparticles in the shape of sphere, hydrothermal synthesis was used, wherein chloroauric acid ($HAuCl_4$), the precursor, was heated in the presence of sodium citrate as a surface stabilizer. The size of the nanoparticle could be regulated by controlling the amount of the surface stabilizer. The method to synthesize nanoparticles in the shape of sphere having the diameter of 20 nm is as follows:

1 g of HAuCl$_4$ was dissolved in 20 ml of distilled water, resulting in the stock solution. 1 g of sodium citrate was dissolved in 100 ml of distilled water. 0.2 ml of the HAuCl$_4$ stock solution was loaded in 198.27 ml of distilled water, which was heated with stirring until it was boiling. When the solution started boiling, 1.53 ml of citrate solution was added thereto. Then, the color of the solution turned from light yellow into dark gray. When reduction was fully induced, the color turned into purple. Then, the heating had to be stopped. The solution was cooled down at room temperature.

<1-2> Synthesis of Gold Nanoparticles in the Shape of Rod

To prepare gold nanoparticles in the shape of rod, HAuCl$_4$ was used as a precursor and cetyltrimethylammonium bromide (CTAB) was used as a surface stabilizer. As a reducing agent, NaBH$_4$ was used. As a result, small gold nanoparticles were prepared. Then, the small gold nanoparticles were grown by the seed-mediated growth method using silver ions and ascorbic acid. The synthesis method is described in more detail hereinafter.

In step 1, gold nanoparticles in the shape of sphere having the diameter of 5 nm were prepared. 100 mM HAuCl$_4$ stock solution and 10 mM NaBH$_4$ solution were prepared. NaBH$_4$ solution stood at 0° C. for at least 1 hour for the activation. 2.2 g of CTAB was loaded in 40 ml of distilled water, followed by full stirring. 100 ml of HAuCl$_4$ stock solution was added thereto, followed by further stirring for 1 hour. 2.4 ml of NaBH$_4$ solution was added thereto and the mixture was stirred vigorously for 2 minutes. The mixture stood at room temperature for at least 3 hours and then used.

The growth solution was prepared by adding 3.64 g of CTAB to 99.5 ml of distilled water with full stirring. 500 ml of HAuCl$_4$ stock solution was added thereto, followed by further stirring. 0.03 g of AgNO$_3$ was dissolved in 25 ml of distilled water, from which 1 ml was taken and added to the above. 0.24 g of ascorbic acid acting as a reducing agent was dissolved in 10 ml of distilled water. 700 ml of the ascorbic acid solution was added to the above. Then, trivalent gold ions (Au$^{3+}$) were reduced to 0 valent ions during which the color turned into transparent.

80 ml of the gold nanoparticle seed solution prepared in step 1 was added to the growth solution, which stood for overnight without any stimulation or shock. Then, the gold nanoparticles of 5 nm in the diameter would grow to be the gold nanoparticles in the shape of rod. The length of the gold nanoparticle in the shape of rod could be regulated by adjusting the amount of CTAB and AgNO$_3$.

<1-3> Synthesis of Gold Nanoparticles in the Shape of Star

To prepare gold nanoparticles in the shape of star, the gold nanoparticles in the shape of sphere, the seed particles at that time, were grown by the seed-mediated growth method. HAuCl$_4$ was used as a precursor and sodium citrate was used as a surface stabilizer. Glycerol was additionally used. As a result, monodispersed nanoparticle solution was prepared. The method is described in more detail hereinafter.

First, the solutions of gold nanoparticles in the shape of sphere having different diameters of 5, 10, 20, 40, 50, and 100 nm were prepared. As described hereinbefore, HAuCl$_4$ was used as a precursor and sodium citrate was used as a surface stabilizer according to the hydrothermal synthesis method. The size of gold nanoparticle was regulated by adjusting the amount of the surface stabilizer. The prepared gold nanoparticle solution was cooled down at room temperature, which was used as a seed solution for the synthesis of gold nanoparticles in the shape of star.

300 ml of the gold nanoparticle seed solution and 1 ml of glycerol were added to 9.8 ml of distilled water, followed by full stirring. 5 minutes later, 22 ml of 1% sodium citrate, 100 ml of 1% HAuCl$_4$, and 42.5 ml of 0.1% AgNO$_3$ were mixed, resulting in a growth solution. The growth solution was added quickly to the above. 100 ml of 1% hydroquinone solution was added thereto right away. Once the stirring was stopped, the color of the solution turned into indigo blue from red in a few minutes.

The gold nanoparticles in the shape of sphere and the gold nanoparticles in the shape of star were synthesized by using the surface stabilizer having carboxyl group, so that the additional surface treatment was not necessary. In the meantime, the gold nanoparticles in the shape of rod were prepared by using CTAB (cetyltrimethylammonium bromide) having positive charge as a surface stabilizer, so that the particles were coated with carboxyl group-rich PAA (polyacrylic acid) (FIG. 7B). Nanoparticles could be prepared by diverse surface treatment methods shown in FIG. 7A and FIGS. 7C-7H in addition to PAA coating.

As a result, as shown in FIG. 6, gold nanoparticles in the shape of sphere having the diameters of 5, 10, 15, 18, 20, 50, and 100 nm, gold nanoparticles in the shape of rod having the sizes of 15×36 and 15×55.5 nm, gold nanoparticles in the shape of star having the diameters of 15, 30, 60, 125, and 230 nm were synthesized (FIG. 6).

Experimental Example 1: Crystallization of *Bacillus subtilis* YesR Protein Using Gold Nanoparticles Crystallization of *Bacillus subtilis* YesR protein having his-tag at amino terminal was performed using the gold nanoparticles synthesized in Examples <1-1> and <1-2>.

Particularly, *Bacillus subtilis* YesR protein at the concentration of 5.6 mg/ml was dissolved in the buffer composed of 20 mM Tris-HCL (pH 7.5), 200 mM NaCl, and 1 mM NiCl$_2$. A 96-well sitting drop plate was used for the crystallization of protein (FIG. 8). As shown in FIG. 9 and FIG. 10, 70 ml of MCSG 2T (96 conditions), the crystallization solution provided by Microlytic, was loaded in each well. 0.5 ml of the crystallization solution was mixed with 0.5 ml of the protein solution containing 10$^4$ gold nanoparticles, which was loaded in a drop, followed by sealing with transparent tape (FIG. 9 and FIG. 10). The prepared plate was stored at 20° C. and the crystallization was observed under microscope.

Figure 11:
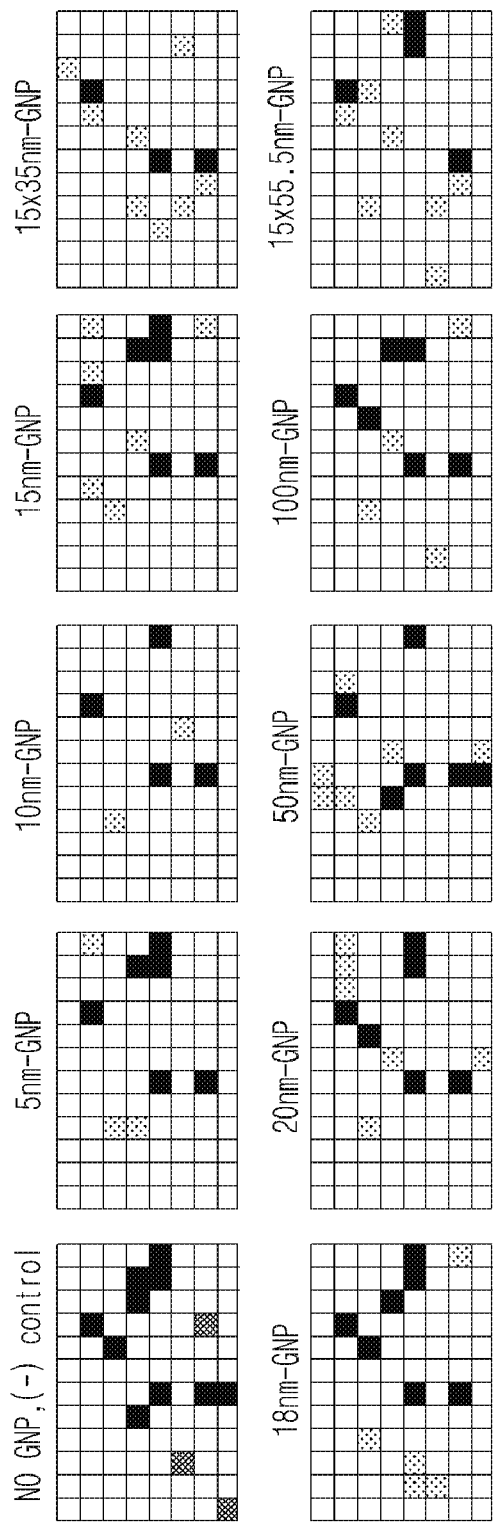
FIG. 11 is a diagram illustrating the crystallization conditions when gold nanoparticles in different sizes and shapes were used for the crystallization of *Bacillus subtilis* YesR protein in 96 MCSG-2T crystallization solutions and when the control without gold nanoparticles was used. Conditions that generated crystals both in control and in the presence of gold nanoparticles are colored black. Conditions that generated crystals only in control are colored dark grey. Conditions that generated crystals only in the presence of gold nanoparticles are colored light grey.
Figure 12:
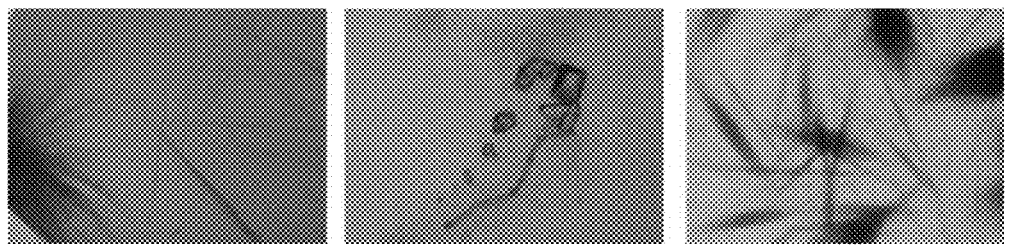
FIG. 12 is a diagram illustrating the crystals generated from the protein crystallization in the presence of gold nanoparticles.
Figure 13:
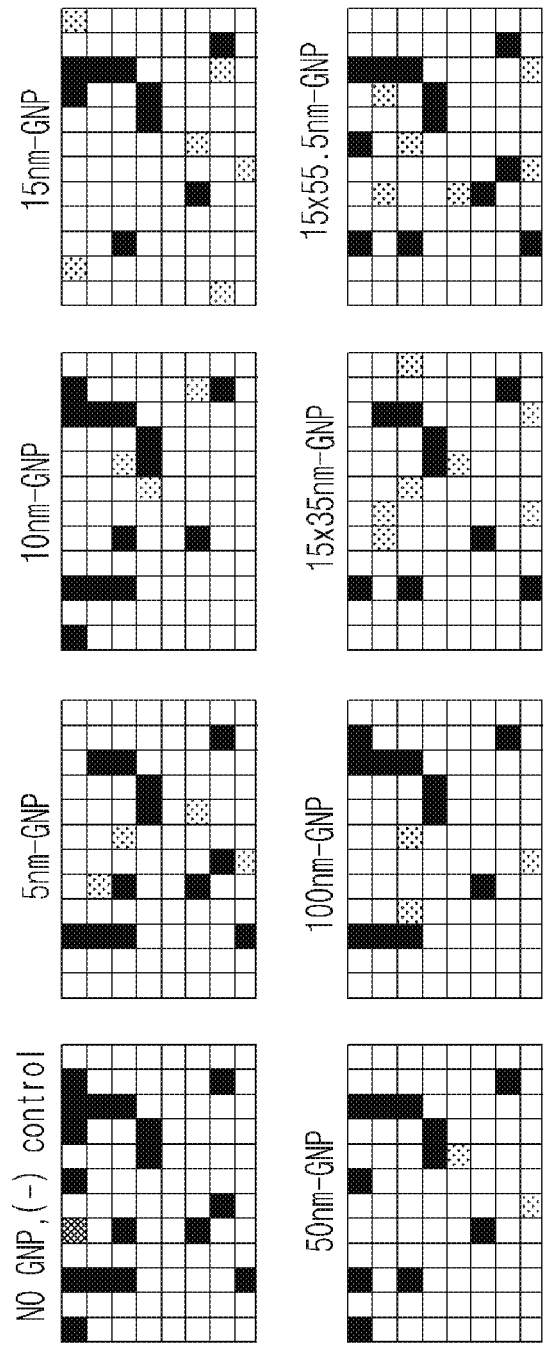
FIG. 13 is a diagram illustrating the crystallization conditions when gold nanoparticles in different sizes and shapes were used for the crystallization of chicken egg white lysozyme in 96 MCSG-2T crystallization solutions and when the control without gold nanoparticles was used.
Figure 14:
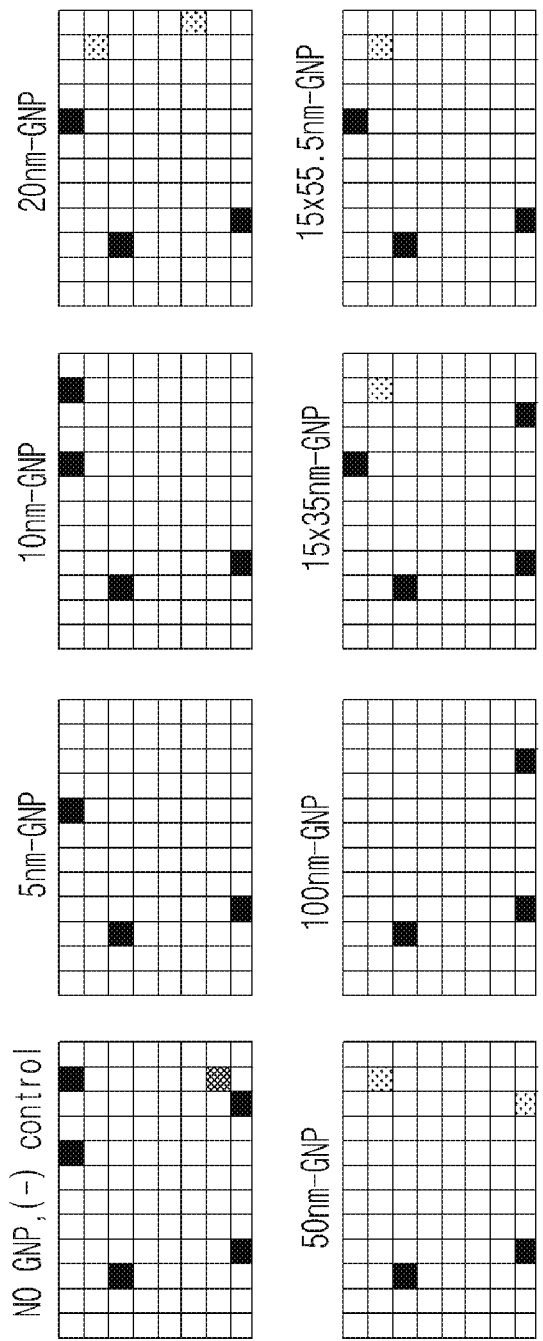
FIG. 14 is a diagram illustrating the crystallization conditions when gold nanoparticles in different sizes and shapes were used for the crystallization of bovine serum albumin in 96 MCSG-2T crystallization solutions and when the control without gold nanoparticles was used.
Figure 15:
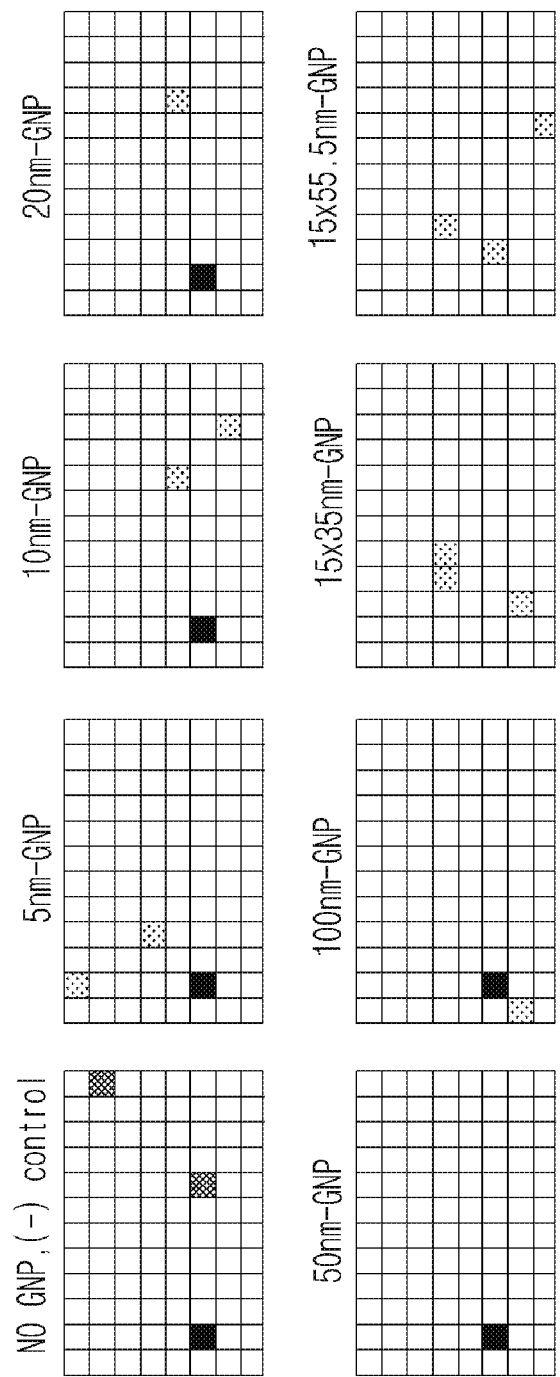
FIG. 15 is a diagram illustrating the crystallization conditions when gold nanoparticles in different sizes and shapes were used for the crystallization of *alicyclobacillus acidocaldarius* acetyl-CoA carboxylase in 96 MCSG-2T crystallization solutions and when the control without gold nanoparticles was used.
Figure 16:
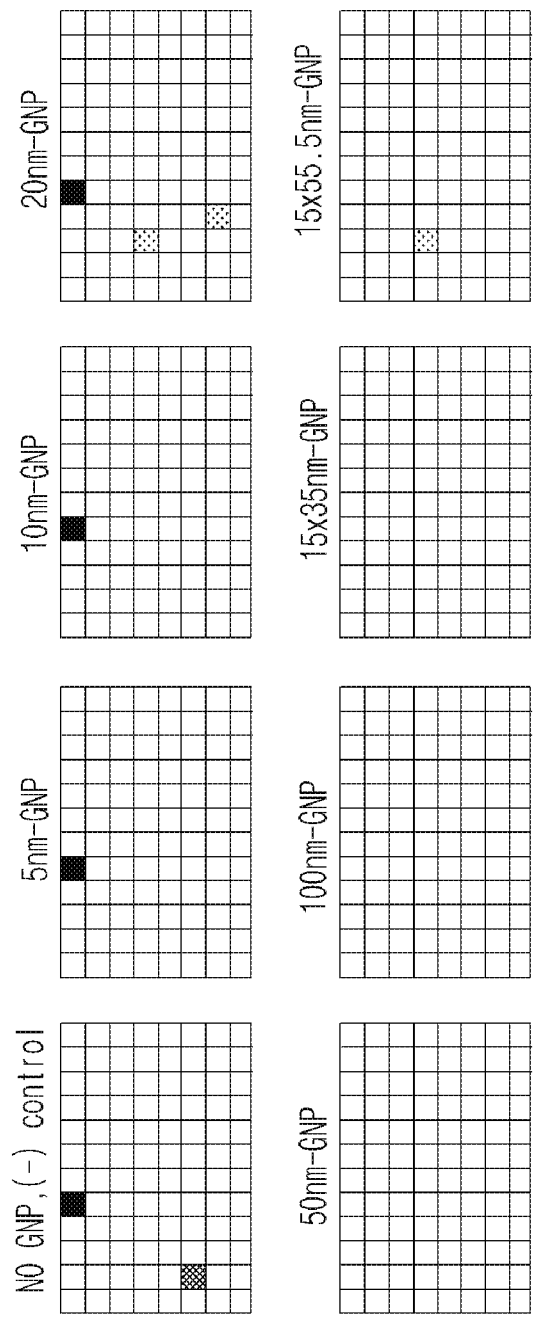
FIG. 16 is a diagram illustrating the crystallization conditions when gold nanoparticles in different sizes and shapes were used for the crystallization of *listeria monocytogenes* hypothetical protein in 96 MCSG-2T crystallization solutions and when the control without gold nanoparticles was used.

As a result, as shown in FIG. 11, crystallization was all observed in the control not added with gold nanoparticles and in the 96-well plate added with 9 kinds of gold nanoparticles (gold nanoparticles in the shape of sphere having the diameters of 5, 10, 15, 18, 20, 50, and 100 nm and in the shape of rod having the size of 15×36 and 15×55.5 nm). In FIG. 10, the part designated with black indicates that the crystallization was induced both in the control and in the presence of gold nanoparticles. The part designated with light grey indicates that the crystallization was only induced in the presence of gold nanoparticles. The part designated with dark grey indicates that the crystallization was only induced in the control (FIG. 11). The 9 different gold nanoparticles required different crystallization conditions among each other and 25 all new crystallization conditions were confirmed from those 9 different gold nanoparticles (38 conditions in total). Considering the crystallization conditions for the control were 13, the chance of successful crystallization of *Bacillus subtilis* YesR protein with gold nanoparticles was significantly increased, which suggested that gold nanoparticles played an important role in nucleation necessary for the crystallization. The protein crystals were grown in the shape of needle and rectangle as well, as shown in FIG. 12.

Experimental Example 2: Crystallization of Protein Using Gold Nanoparticles

Crystallization of four proteins having his-tag at amino terminal (chicken egg white lysozyme, bovine serum albumin, *Alicyclobacillus acidocaldarius* acetyl-CoA carboxylase, and *Listeria monocytogenes* hypothetical protein) was performed using the gold nanoparticles synthesized in Examples <1-1> and <1-2>.

Particularly, the proteins used herein were chicken egg white lysozyme (7.8 mg/ml), Bovine serum albumin (13.4 mg/ml), *Alicyclobacillus acidocaldarius* acetyl-CoA carboxylase (13.6 mg/ml), and *Listeria monocytogenes* hypothetical protein (12.1 mg/ml). These proteins were dissolved in the buffer composed of 20 mM Tris-HCL (pH 7.5), 200 mM NaCl, and 1 mM $NiCl_2$. A 96-well sitting drop plate was used for the crystallization of protein (FIG. 8). As shown in FIG. 9 and FIG. 10, 70 ml of MCSG 2T (96 conditions), the crystallization solution provided by Microlytic, was loaded in each well. 0.5 ml of the crystallization solution was mixed with 0.5 ml of the protein solution containing gold nanoparticles ($2 \times 10^7$ particles/ml), resulting in the preparation of 1.0 ml drop. 10,000 gold nanoparticles were included in a drop, and the plate was sealed with transparent tape (FIG. 9 and FIG. 10). The prepared plate was stored at 20° C. and the crystallization was observed under microscope.

As a result, as shown in FIGS. 13~16, crystallization was all observed in the control not added with gold nanoparticles and in the 96-well plate added with kinds of gold nanoparticles (gold nanoparticles in the shape of sphere having the diameters of 5, 10, 20, 50, and 100 nm and in the shape of rod having the size of 15×36 and 15×55.5 nm). In FIGS. 13~16, the part designated with black indicates that the crystallization was induced in the control and in the presence of gold nanoparticles. The part designated with light grey indicates that the crystallization was only induced in the presence of gold nanoparticles. The part designated with dark grey indicates that the crystallization was only induced in the control (FIGS. 13~16). The 7 different gold nanoparticles required all different crystallization conditions. Precisely, the crystallization conditions confirmed by 4 proteins (chicken egg white lysozyme, bovine serum albumin, *Alicyclobacillus acidocaldarius* acetyl-CoA carboxylase, and *Listeria monocytogenes* hypothetical protein) were respectively 18, 6, 3, and 2 for the control and 19, 2, 8, and 2 in the presence of gold nanoparticles (total 37, 8, 11, and 4 conditions). That means gold nanoparticles significantly increased the chance of successful crystallization of protein.

As explained hereinbefore, the addition of gold nanoparticles brought the effect of increasing the crystallization conditions for the 5 proteins used herein, and induced nucleation of protein with increasing the chance of crystallization of protein.

Experimental Example 3: Crystallization of Protein Using Gold Nanoparticles in the Shape of Star Crystallization of chicken egg white lysozyme having his-tag at amino terminal was additionally induced with the gold nanoparticles in the shape of star synthesized in Example <1-3>.

Particularly, the protein, chicken egg white lysozyme (7.8 mg/ml), was dissolved in the buffer composed of 20 mM Tris-HCl (pH 7.5), 200 mM NaCl, and 1 mM $NiCl_2$. A 96-well sitting drop plate was used for the crystallization of protein (FIG. 8). As shown in FIG. 9 and FIG. 10, 70 ml of MCSG 2T (96 conditions), the crystallization solution provided by Microlytic, was loaded in each well. 0.5 ml of the crystallization solution was mixed with 0.5 ml of the protein solution containing gold nanoparticles ($2 \times 10^7$ particles/ml), resulting in the preparation of 1.0 ml drop. 10,000 gold nanoparticles were included in a drop, and the plate was sealed with transparent tape (FIG. 9 and FIG. 10). The prepared plate was stored at 20° C. and the crystallization was observed under microscope.

Figure 17:
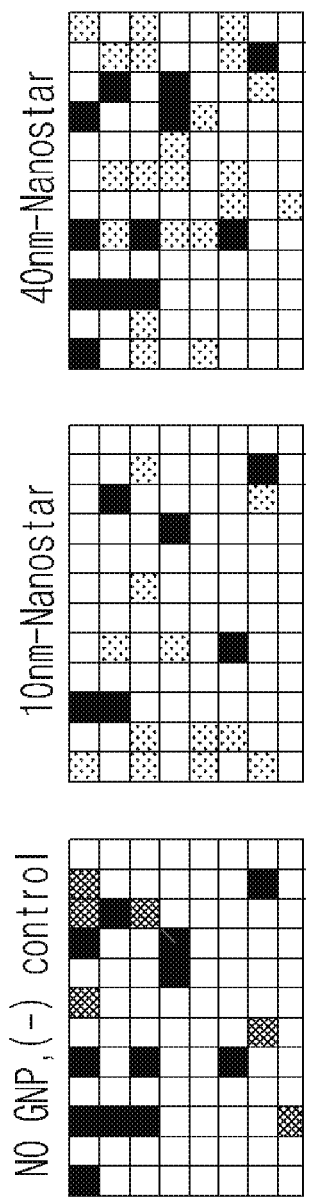
FIG. 17 is a diagram illustrating the crystallization conditions when two different kinds of gold nanoparticles in star shape were used for the crystallization of chicken egg white lysozyme in 96 MCSG-2T crystallization solutions and when the control without gold nanoparticles was

As a result, as shown in FIG. 17, crystallization was all observed in the control not added with gold nanoparticles and in the 96-well plate added with 2 kinds of gold nanoparticles in the shape of star having the diameters of 30 and 125 nm. In FIG. 17, the part designated with blue indicates that the crystallization was induced in the control and in the plate added with gold nanoparticles. The part designated with red indicates that the crystallization was only induced in the presence of gold nanoparticles. The part designated with yellow indicates that the crystallization was only induced in the control (FIG. 17). The 2 different gold nanoparticles required different crystallization conditions and 25 all new crystallization conditions were confirmed from those 2 different gold nanoparticles. Considering the crystallization conditions for the control were 18, the above results indicated that gold nanoparticles could significantly increase the chance of successful crystallization of protein.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for inducing nucleation for the crystallization of protein which includes the step of mixing the nanoparticles coated with carboxyl group with the protein having his-tag in the presence of $Ni^{2+}$ ions.

2. The method for inducing nucleation for the crystallization of protein according to claim 1, wherein the nanoparticles are selected from the group consisting of platinum nanoparticles, silver nanoparticles, magnetic nanoparticles, polymer nanoparticles, and gold nanoparticles.

3. The method for inducing nucleation for the crystallization of protein according to claim 2, wherein the nanoparticles are gold nanoparticles.

4. The method for inducing nucleation for the crystallization of protein according to claim 1, wherein the surface of nanoparticle is coated with carboxyl group using a carboxyl group-rich organic molecule.

5. The method for inducing nucleation for the crystallization of protein according to claim 4, wherein the carboxyl group-rich organic molecule is selected from the group consisting of citrate, mercapundecanoic acid (MUA), mercaptopropionic acid (MPA), poly acrylic acid (PAA), glutathione (GSH), thioglycolic acid (TGA), cysteine, mercaptobenzoic acid, D-penicillamine, and dihydrolipoic acid (DHLA).

6. The method for inducing nucleation for the crystallization of protein according to claim 1, wherein the nanoparticle is in one of those shapes selected from the group consisting of sphere, rod, and star shapes.

7. The method for inducing nucleation for the crystallization of protein according to claim 6, wherein the nanoparticles in the shape of sphere are 5~100 nm in diameter, those in the shape of rod are 36~55.5 nm in length and 15 nm in diameter, and those in the shape of star are 15~230 nm in diameter.

8. The method for inducing nucleation for the crystallization of protein according to claim 1, wherein the number of nanoparticles used for the crystallization of protein is $10^3$~$10^7$.

9. The method for inducing nucleation for the crystallization of protein according to claim 1, wherein the protein is selected from the group consisting of those proteins having his-tag.

10. The method for inducing nucleation for the crystallization of protein according to claim 1, wherein the count rate of proteins and nanoparticles are $1:10^7$~$1:10^{13}$.

11. A method for inducing selective binding of protein for the crystallization of protein which contains the step of mixing the nanoparticles coated with carboxyl group and the proteins having his-tag in the presence of $Ni^{2+}$ ions.

12. A kit for the crystallization of protein containing the followings:
  1) a resin mixed with nanoparticles coated with carboxyl group containing $Ni^{2+}$; and
  2) a protein having his-tag on the surface thereof.

* * * * *